(12) United States Patent
De Paep

(10) Patent No.: US 7,801,616 B2
(45) Date of Patent: Sep. 21, 2010

(54) TECHNICAL SERVICE DIAGNOSTIC TOOL FOR A SOUND PROCESSOR

(75) Inventor: Patrik De Paep, Lokeren (BE)

(73) Assignee: Cochlear Limited, Lane Cove (AU)

( * ) Notice: Subject to any disclaimer, the term of this patent is extended or adjusted under 35 U.S.C. 154(b) by 1385 days.

(21) Appl. No.: 10/503,492

(22) PCT Filed: Feb. 10, 2003

(86) PCT No.: PCT/AU03/00138

§ 371 (c)(1),
(2), (4) Date: Dec. 29, 2004

(87) PCT Pub. No.: WO03/067925

PCT Pub. Date: Aug. 14, 2003

(65) Prior Publication Data

US 2005/0113884 A1 May 26, 2005

(30) Foreign Application Priority Data

Feb. 8, 2002 (AU) .................................. PS0434

(51) Int. Cl.
*A61N 1/00* (2006.01)
(52) U.S. Cl. ........................................ 607/57
(58) Field of Classification Search .................. 607/30, 607/55–57, 59, 60; 702/103; 381/315, 60; 600/300
See application file for complete search history.

(56) References Cited

U.S. PATENT DOCUMENTS

| 4,471,171 | A | * | 9/1984 | K/o/ pke et al. ................ 381/60 |
| 4,992,966 | A | * | 2/1991 | Widin et al. ................ 702/103 |
| 5,303,306 | A | * | 4/1994 | Brillhart et al. ............. 381/315 |
| 5,584,869 | A | | 12/1996 | Heck et al. |
| 6,118,877 | A | * | 9/2000 | Lindemann et al. ........... 381/60 |
| 6,334,072 | B1 | | 12/2001 | Leysieffer |
| 6,402,689 | B1 | * | 6/2002 | Scarantino et al. .......... 600/300 |
| 7,096,067 | B2 | * | 8/2006 | Linberg ....................... 607/30 |
| 7,110,822 | B1 | * | 9/2006 | Palmer ........................ 607/57 |

* cited by examiner

*Primary Examiner*—George Manuel
(74) *Attorney, Agent, or Firm*—Kilpatrick Stockton, LLP

(57) ABSTRACT

Diagnosis means, in the form of a software tool, for on-site diagnosis of a sound processor of an implanted prosthesis. The diagnosis means assesses hardware components and programming functions of the sound processor and accesses and assesses patient data stored in the sound processor. An activity log or report based on the assessment is available. Updated data and functions pertaining to a patient are retrieved and applied to the diagnosis means. The diagnosis means can replace the patient data and/or programming functions of the sound processor in the event of patient data corruption or programming function error in the sound processor. A method of on-site diagnosis of a sound processor and a process for diagnosis and repair of a sound processor of an implanted prosthesis are also disclosed.

40 Claims, 2 Drawing Sheets

TECHNICAL SERVICE DIAGNOSTIC TOOL FOR A SOUND PROCESSOR

CROSS-REFERENCE TO RELATED APPLICATIONS

This application is a national stage application and claims the priority of PCT/AU2003/000138, filed on Feb. 10, 2003, which claims the priority of Australian Provisional No. PS 0434, filed on Feb. 8, 2002. The entire disclosure and contents of the above patents and applications are hereby incorporated by reference.

FIELD OF THE INVENTION

The present invention relates to the diagnosis and technical servicing of a sound processor for a prosthesis, and in particular to a tool to assist in diagnosing, analysing, servicing and initialising a sound processor for a cochlear implant.

DESCRIPTION OF THE PRIOR ART

Hearing aids and cochlear implants have been proven to be useful in restoring the sensation of hearing to hearing impaired individuals.

In cases of mild hearing loss, wherein the essential structures of the cochlea are intact and the hair cells are able to detect the mechanical vibration of the cochlea fluid and transfer this into a neural impulse detected by the brain as sound, hearing aids are commonly used. Such hearing aids typically magnify the sound normally heard by the individual so that the individual experiences this sound sensation at an equivalent level to that experienced by a normal hearing listener.

In cases where the hair cells of the cochlea have been damaged to the extent that they are no longer able to transfer the mechanical vibration of the cochlea fluid into an electrical signal, traditional hearing aids are of no use. In such situations where there is a severe or profound hearing loss, cochlea implants have been developed to restore the function of hearing to affected individuals. One such implant is described in U.S. Pat. No. 4,532,930, the contents of which are incorporated herein by reference. The cochlear implant bypasses the role of the hair cells and directly delivers electrical stimulation to the nerves in the cochlea, representative of speech and environmental sounds, with the neural impulses generated by such electrical signals being sent to the brain and being interpreted as sound. The electrical stimulation is usually delivered to selected nerve sites within the cochlea by an array of electrodes, electrically connected to an implanted stimulator device.

Traditionally, the implanted stimulator device receives a coded sound signal from an external sound processor device and from this coded signal the implanted stimulator directs the appropriate electrical stimulation to be provided to the appropriate electrode to reproduce the corresponding sound. The implanted stimulator is equipped with electronic circuitry and switches to allow stimulation to be delivered to a number of electrodes simultaneously or in very quick succession to provide detailed sound perception.

The external sound processor provides the coded signal to the implanted stimulator via a transcutaneous link, such as an RF link, and the coded signal is directly representative of the surrounding sound as detected by an external microphone. The external microphone may be mounted on the external sound processor or may be remote from the external sound processor but connected via a suitable link.

With continuing technological advancements, it may be possible to provide a system which is totally implantable within the head of the user, such that an internal microphone is capable of detecting the external environmental sounds. In such a system the sound processor would also be implanted within the head of the user and process the sound signal in much the same way as the previously described system.

In such a system, the basic function of the sound processor is to take an audio signal from a microphone and to process it according to a particular speech coding strategy, to produce a signal that contains stimulation information for the implant. In earlier speech coding strategies, the processor attempted to identify the important sounds present in the signal (such as speech) and encode them as patterns of electrical stimulation. In more recent strategies, the full range of spectral and temporal information in the audio signal has been provided to the user without any attempt by the processor to fit it into a preconceived mould.

In general, speech processors are quite patient specific and whilst the system hardware is relatively common for all users, the software used as well as the benefits gained for different software packages varies considerably from patient to patient. This is due in the main to the fact that the degree of deafness and structures of the cochlea are different from individual to individual and depend greatly on the cause of the deafness as well. Therefore the speech processors need to take into consideration such user variations and appreciate that stimulation of a specific amplitude on a specific electrode for one individual will cause a completely different sensation to the same stimulation of another individual. Hence, specific user parameters form an important part of most speech coding strategies.

It is important to then realise that in providing cochlear implants and in supporting the continual use of such implants, there will always be a need to deal with each user on an individual basis to ensure that they are receiving maximum benefit from the device.

This becomes particularly important following the implantation of a cochlear implant, and in the follow up support and service that accompanies such a procedure. Typically, following the surgical implantation of a device the user must have the device correctly fitted or programmed to ensure that the operation of the device is modified to take into consideration individual characteristics, such as active/inactive electrodes and individual comfort and threshold levels for each channel of stimulation.

Over time and as the brain and body adjust to the implant it may be necessary to further modify the user parameters to maintain optimum performance of the implant, and it is important that such services are provided over the lifetime of the individual. As well as adjusting and creating patient specific individual user stimulation maps, it is also important that support is provided should any problems occur with the device hardware. Such a support service is crucial and needs to be organised and detailed enough to ensure that any problems and difficulties that affect the performance of the device are dealt with swiftly and efficiently to ensure that the user does not experience extended periods of inoperation.

Experience has shown that the cause of malfunctions is often hard to pinpoint, and in order to correctly diagnose problems a good knowledge of all the functionality of the device is required, together with a considerable amount of experience with such devices. The reason for this is that any perceived problem could be a direct consequence of the variety of elements that influence the device performance, for example, the device hardware, the embedded software, the installed software, the coding strategies used and also the recipient specific parameters (such as stimulation maps and the like).

At present, in the unfortunate event of a user experiencing a difficulty or malfunction that causes them to lose system functionality, the user needs to contact a local clinic/agent who has been assigned to deal with such issues. This clinic/agent is usually familiar with the individual's needs and requirements and has full records of the patient specific parameters of the associated speech processing strategies. Should an individual experience a problem it is the role of the clinic/agent to attend with this problem and rectify it as soon as possible so that the user experiences minimal inconvenience. Quite often this problem may reside in faulty connection of leads or battery terminals, and can be merely rectified by replacing the faulty leads or batteries, without requiring any further action.

Should a fault occur with an individual's external sound processor, rendering the device ineffective, the problem becomes more serious. In such instances the sound processor must be fully checked by the manufacturer or an authorised agent of the manufacturer, and as such it is likely that the speech processor must be taken from the patient and shipped to such a repair area. In such instances the clinic/agent issues the user with a temporary replacement device and loads the patient speech coding algorithms and the patient parameter settings into the replacement device so that the implant can function properly whilst the user's own device is being investigated and repaired.

Whilst all effort is made to protect against device malfunctions, with electronic devices such as an external speech processor, it is difficult to ensure that malfunctions will not occur due to the nature of the device and the amount of use such a device receives. Also as the sound processor is responsible for coding the stimulation information to be delivered by the implanted stimulator, it is important that any system malfunction is fully investigated to ensure that the user does not receive improper stimulation which may have adverse effects. This is why all sound processor problems are sent to the supplier or manufacturer to investigate and report to ensure the integrity of all devices returned.

Nevertheless, it has been found that a large number of speech processors (20-25%) that have been reported as being malfunctions/faulty and returned to the supplier or manufacturer for investigation have been found to have no mechanical or electrical problems and function normally when tested. In such instances the problems have resided in corrupted patient data or programming data stored on the sound processor. This may have occurred as a result of the sound processor being exposed to abnormal environmental conditions, such as extreme electrical, magnetic, thermal, mechanical or chemical forces, or even as a result of an inadvertent power failure or batteries being replaced in an incorrect manner.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY OF THE INVENTION

According to a first aspect, the present invention provides a method for on site diagnosis of a processor of an implantable prosthesis, the method comprising the steps of:

testing functionality of a hardware component of the processor;

assessing data stored by the processor; and assessing software functions of the processor.

By undertaking such assessment steps on-site, the present invention enables a recipient, clinician or the like to determine whether or not a perceived fault is in fact a fault requiring dispatch of the processor to a repair facility. As noted previously, perhaps 20%-25% of perceived faults do not require dispatch of the processor to a repair facility, and the present invention provides a manner in which an assessment of the fault perceived by the recipient can be carried out on site and if possible, rectified on-site, prior to dispatch of the processor to the repair facility. Even in cases in which a fault exists requiring dispatch of the processor to a repair facility, the present invention enables closer identification of the fault to be obtained on site, which can be provided to the repair facility along with the sound processor to ease the task of the repair facility.

It is to be understood that on-site diagnosis in accordance with the present invention involves diagnosis of the sound processor remote from a repair facility provided by, for example, a manufacturer. Such on-site diagnosis may comprise diagnosis by a recipient of the implant at their own home, or may comprise diagnosis by a clinician at a clinic.

The present invention preferably further comprises one or more of the steps of:

restoring functionality of the sound processor;

reporting on performance of the sound processor; and checking the effectiveness of restored functions of the sound processor.

In particular, the step of restoring functionality of the sound processor may comprise one or more of the following:

restoring software functions of the processor; and restoring data stored by the sound processor.

Similarly, the step of reporting on performance of the sound processor may comprise assembling an activity log with performed functions, errors and warnings, and reporting the activity log to a predetermined recipient. The activity log may assemble the functions errors and warnings at several levels of detail, and may report at a level of detail which corresponds to the predetermined recipient of the activity log. That is, depending on the identity of the predetermined recipient of the activity log, such as the implant recipient, the clinician, or the implant manufacturer, the level of detail of each of the elements of the activity log may be varied accordingly.

Preferably, the method of the present invention further comprises the step of prior to assessing and testing the sound processor, checking for updated assessment methodology. For instance, such a step may comprise checking for new data to be installed to the sound processor, or checking for new software functions to be installed to the sound processor. Such a step provides for "self-updating" of the method of the present invention, for example by requesting a repair facility or implant manufacturer whether such new data or software functions exist. Such a step may be performed over the internet, and may be performed by a diagnosis tool without user intervention so as to provide automated self updating.

In accordance with the present invention, correct diagnosis of the problem on-site could significantly reduce the repair time and avoid the need to send the processor a long distance to a repair facility for a full analysis, when the fault could be repaired on the spot by reloading the associated data onto the processor, followed by a full functional analysis. Further, by performing a detailed diagnosis and possible device repair at the user's own home or at the clinician's initial point of contact with the user, the total disruption experienced by the user could be significantly reduced.

Even further, by allowing a detailed diagnosis of the device to occur immediately when the device is thought to malfunction, either directly by the recipient themself, or when the device has been received by the clinic/agent, an immediate indication of the type of problem experienced and the likely time such a problem would take to repair can be provided to the recipient. Additionally, this repair time would most likely be further reduced as the supplier repair team would be presented with a relatively detailed diagnosis report which would point to the source of the problem, without having to perform a full diagnostic check to isolate the problem.

In addition to the above mentioned time savings, there are further time savings achievable and increased recipient satisfaction by allowing the recipient to perform self diagnosis and rectification of minor problems such as restoration of coding strategies and recipient parameters, themselves, without the need to visit a specialist or dedicated clinic.

Preferably, the method of the present invention further enables on-site rectification of at least some faults to be performed. Accordingly the method of the present invention preferably further comprises, in the event of patient data corruption in the speech processor, retrieving a backup copy of the patient data and replacing the patient data of the processor. The step of retrieving the backup data may comprise retrieving the backup data from a floppy disk, CD ROM or the like kept by the patient, or alternatively may comprise retrieving the backup patient data from a central data storage maintained, for example, by a producer of the prosthesis, or by a repair facility to which the processor would otherwise be sent. Alternatively, the step of retrieving may comprise retrieving the backup patient data from a local storage means such as a clinician's personal computer or the recipient's personal computer. The step of retrieving may comprise retrieving the backup copy of the patient data locally, or retrieving the backup copy over a network, such as the internet Similarly, the method of the present invention preferably further comprises, in the event of programming function error in the processor, reinstalling the programming functions to the processor. Again, the programming functions may be retrieved from a floppy disk or CD ROM or the like kept by the patient, or from a central data repository maintained, for instance, by a maker of the prosthesis. Alternatively the programming functions may be retrieved from an on site storage device, such as a clinician's personal computer. In the event of programming function error in the processor, the identified error is preferably referred back to an implant manufacturer or a repair facility, and is preferably referred back to a rehabilitation centre associated with the recipient of the implant. In the event of a detection that the programming functions of the processor deviate from the standard and suspicious programming elements are identified, the present invention preferably signals warnings to the manufacturer and/or repair facility and to the rehabilitation centre, referring the recipient to see their audiologist or clinician, and recommending that the device not be sent to a repair facility for unneeded repair.

According to a second aspect the present invention provides a diagnosis means for on site diagnosis of a processor of an implanted prosthesis, the diagnosis means comprising:

means to assess hardware components of the processor;
means to access and assess stored patient data of the processor; and
means to assess programming functions of the speech processor.

It is envisaged that the diagnosis means will comprise an appropriately programmed and configured computer, able to connect to the processor and carry out the steps of assessment of the processor. Alternatively the diagnosis means may comprise a hand held device having an application specific integrated circuit (ASIC), operable to perform the desired diagnosis steps.

The diagnosis means may assess the processor in order to verify whether a fault perceived by an implant recipient actually exists prior to dispatch of the processor to a clinic or repair facility, and may produce a detailed activity log based on said assessment. The report may be provided to a processor repair facility along with the processor if there is a need to send the processor for repair. Such an activity log may additionally or alternatively be provided to the implant recipient, or to a clinician or rehabilitation centre associated with the implant recipient.

In preferred embodiments of the invention the diagnosis means is further operable to undertake on site correction or repair of certain faults which may arise within the processor. Accordingly, the diagnosis means preferably further comprises means for replacing the patient data of the processor in the event of patient data corruption in the processor. In such embodiments, the diagnosis means is preferably operable to retrieve a back up copy of the patient data from a floppy disk or CD ROM or the like kept by the patient, or from a central data repository maintained, for instance, by a maker of the implanted prosthesis or by a repair facility. Alternatively, the diagnosis means may itself store a copy of the patient data.

The diagnosis means may further comprise means for retrieving updates and applying such updates to the diagnosis means. For example, the means for retrieving updates may communicate with a remote network site maintained, for example, by a repair facility or an implant manufacturer, in order to determine whether the diagnosis means requires updating. The retrieved updates may comprise updated patient data, updated implant software functions, or updated functionality of the diagnosis means itself.

Similarly, the diagnosis means preferably further comprises means for reinstalling the programming functions to the processor in the event of programming function error in the processor. Again, the programming functions may be retrieved by the diagnosis means from a floppy disk or CD ROM or the like kept by the patient, or from a central data repository maintained, for instance, by a maker of the implanted prosthesis or by a repair facility. Alternatively, the diagnosis means may itself store a copy of the programming functions for installation to the processor in the event of programming function error within the processor.

In accordance with the method and diagnosis means of the present invention, the implanted prosthesis may comprise a cochlea implant, and the processor may comprise a sound processor for converting received sounds into an electrical signal to be applied by an implanted stimulator portion of the cochlea implant. In such embodiments, the patient data of the sound processor assessed by the diagnosis means will typically comprise data such as threshold level, comfort level, and the like. The programming functions of the sound processor assessed by the diagnosis means will typically comprise functions for converting received audio sound detected by a microphone associated with the sound processor into electrical stimulation signals to be passed to an implanted stimulation portion of the implant, using such patient data as threshold level, comfort level and the like.

According to a third aspect, the present invention provides a process for diagnosis and repair of a sound processor of an implanted prosthesis, the process comprising:

a recipient of the implanted prosthesis performing an on-site diagnosis of the sound processor using a recipient diagnosis and repair tool;

the recipient repairing identified errors within the capability of the recipient diagnosis and repair tool;

in the event of identifying an error which is not within the repair capability of the recipient's on-site diagnosis and repair tool, a clinician performing an on-site diagnosis of the sound processor using a clinician diagnosis and repair tool;

the clinician repairing identified errors within the capability of the clinician diagnosis and repair tool; and in the event of identifying an error which is not within the repair capability of the clinician diagnosis and repair tool, providing the sound processor to a repair facility.

The present invention further provides for a computer readable memory encoded with data representing a computer program for controlling a computer to execute a procedure according to any one of the method steps herein disclosed.

The present invention also provides for a computer program element comprising computer program code means for controlling a computer to execute a procedure according to any of the method steps herein described.

BRIEF DESCRIPTION OF THE DRAWINGS

Examples of the invention will now be described with reference to the accompanying drawings in which.

DETAILED DESCRIPTION OF THE PREFERRED EMBODIMENTS

Figure 1:
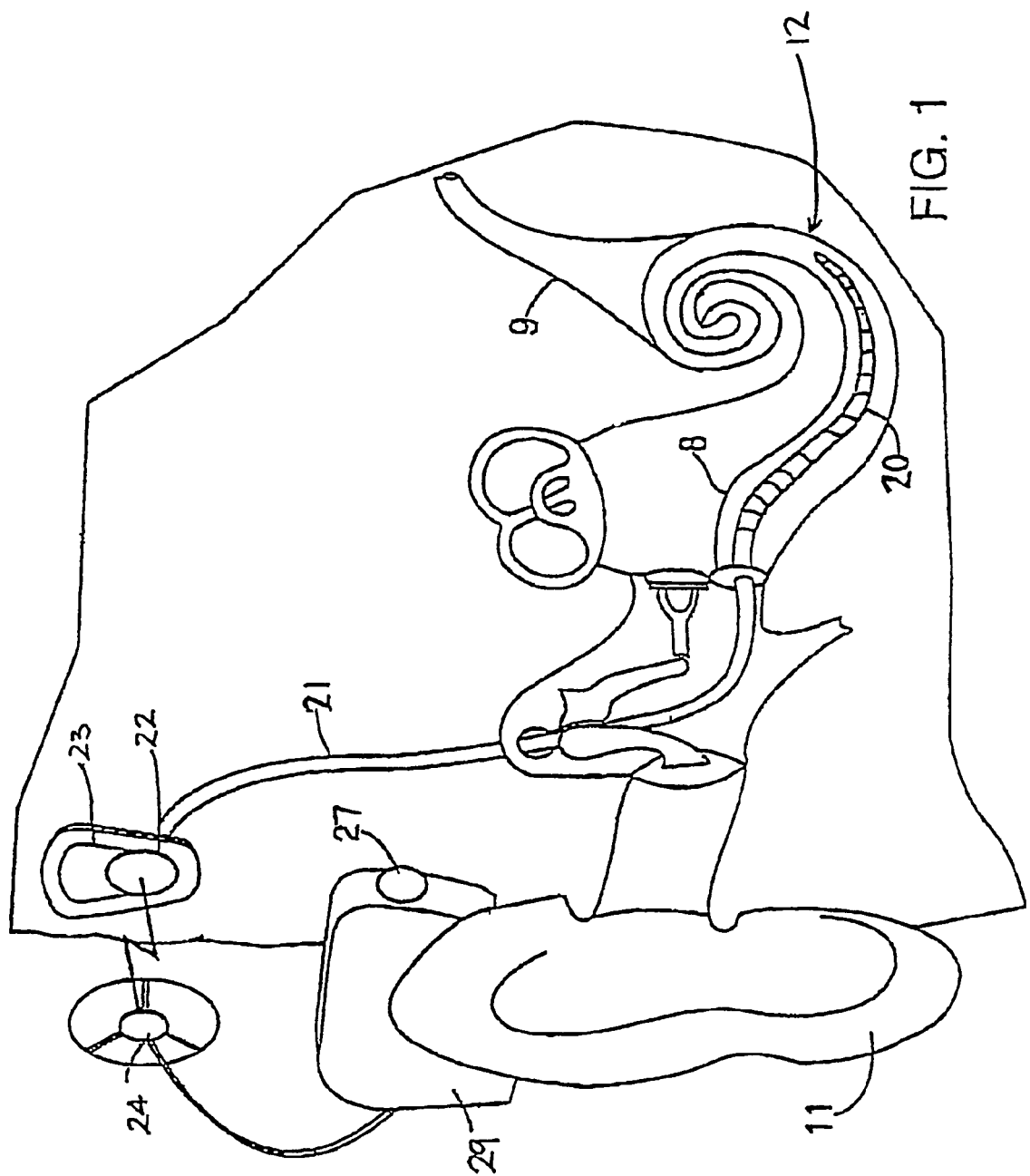
FIG. 1 is a pictorial representation of a cochlear implant system.

Before describing the features of the present invention, it is appropriate to briefly describe the construction of a cochlear implant system with reference to FIG. 1.

Cochlear implants typically consist of two main components, an external component including a sound processor 29, and an internal component including an implanted receiver and stimulator unit 22. The external component includes an on-board microphone 27. The sound processor 29 is, in this illustration, constructed and arranged so that it can fit behind the outer ear 11. Alternative versions may be worn on the body or it may be possible to provide a fully implantable system which incorporates the speech processor and/or microphone into the implanted stimulator unit. Attached to the sound processor 29 is a transmitter coil 24 which transmits electrical signals to the implanted unit 22 via an RF link.

The implanted component includes a receiver coil 23 for receiving power and data from the transmitter coil 24. A cable 21 extends from the implanted receiver and stimulator unit 22 to the cochlea 12 and terminates in an electrode array 20. The signals thus received are applied by the array 20 to the basilar membrane 8 thereby stimulating the auditory nerve 9. The operation of such a device is described, for example, in U.S. Pat. No. 4,532,930.

The sound processor 29 of the cochlear implant can perform an audio spectral analysis of the acoustic signals and outputs channel amplitude levels. The sound processor 29 can also sort the outputs in order of magnitude, or flag the spectral maxima as used in the SPEAK strategy developed by Cochlear Ltd.

Figure 2:
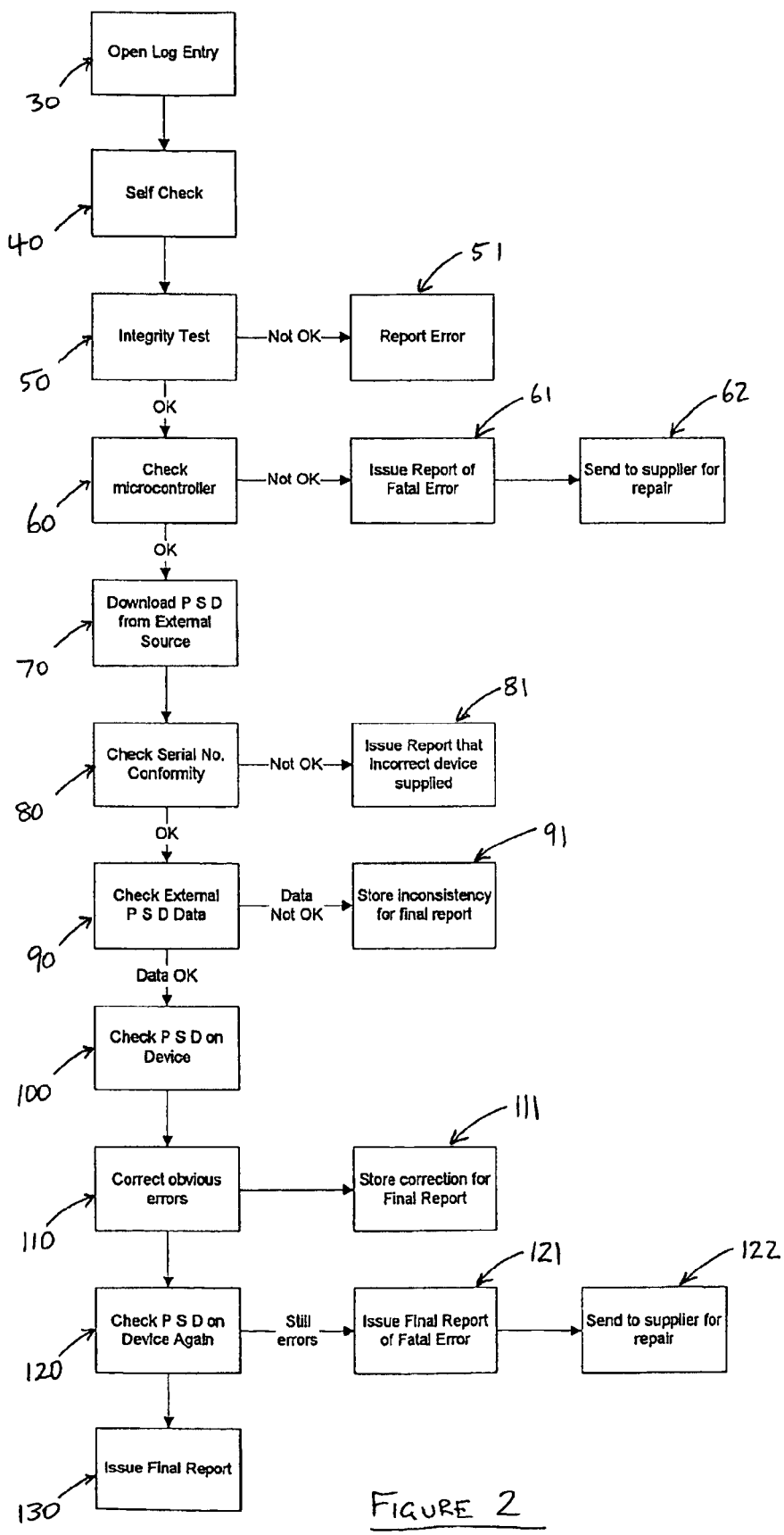
FIG. 2 is a flowchart illustrating a sound processor diagnosis method in accordance with the present invention.

Turning now to FIG. 2, a sound processor diagnosis method in accordance with the present invention is illustrated. In current methods, when a patient experiences a problem with a sound processor they contact their nearest clinic/agent to investigate and correct the problem. Once the clinic has performed an initial superficial check of the processor and assessed that the problem cannot be easily corrected through replacement of the external connector leads or through a faulty connection between leads, the problem is essentially beyond the capabilities of the clinician and needs to be sent back to the original supplier for a more thorough examination.

A replacement device is usually supplied to the individual whilst the device is returned to the supplier for repair and investigation. The replacement device is loaded with the individual's specific individual requirements (maps) and the individual can leave the clinic with a fully functional device whilst they await repair and return of their own device. Except in exceptional circumstances, the individual's own device is always repaired and returned to the individual.

In the first instance, the present embodiment of the invention allows the recipient to check, load and assess their device should a problem/malfunction be evident, or merely as a routine check to ensure that all is in order with the device or to perform regular updates of the device. In the event that a problem exists with the device that the recipient can not rectify, the recipient is then directed to approach a clinician or rehabilitation centre where the matter can be resolved or investigated further, and if required, a replacement device obtained.

The present invention therefore provides a software tool that enables a check, diagnosis, reporting and repair service of perceived faulty sound processors. The software tool assesses the sound processor for fatal errors associated with faulty hardware or with a fatally corrupted volatile memory, software and embedded hardware, and also assesses the sound processor for repairable errors such as one or more altered settings or corrupted stored data, all of which can be repaired by the tool.

FIG. 2 shows a flow chart illustrating operation of the software tool of the present invention. Initially, the sound processor of concern is checked for obvious problems that would affect its functionality, such as faulty batteries, incorrect lead connections and the like. In the event of an obvious problem being found, it is corrected so that a more detailed check of the system can be performed.

The sound processor is then connected to the software tool of the present invention which can be run through a common PC or similar interface.

First, the tool opens a log entry at 30, where all performed functions and outcomes are stored for the particular session. At 40 the tool can perform a self check whereby it searches for any available updates for the device components or for the sound processor function or data libraries. This self check ensures that the device is up to date and contains the most recent system changes applicable for the particular recipient. The self check can interrogate data stored on a central database via the internet or other type of network, wherein the central database contains all system component updates and recipient data updates.

Once the self check 40 has been performed, the tool performs a communication integrity test 50 to assess that the tool is able to communicate with the core of the sound processor, that is, the CPU or micro-controller. Should this integrity test 50 produce an error indicating a problem with the communication channels to the CPU, farther investigation of the device is not possible and the tool at 51 issues a report of a fatal error and advises the recipient that the device must be sent to the manufacturer/supplier for repair. If the integrity test 50 indicates the communication channels are operable, the tool continues the procedure.

Subsequently, at 60, the tool performs an integrity test of the speech processor's micro-controller, by comparing the CPU functionality and its embedded code with the original design code which is known and accessed by the tool from a function library. During this assessment test communication of the main internal components of the sound processor is also addressed. This step essentially resides in the tool accessing specific top level programs from a stored file within a PC or via a central storage database and comparing such programs with those stored on the device. Should there be any inconsistencies found, the tool ceases the test and, at 61, issues a report indicating that a fatal error exists within the microprocessor and suggests that the device be returned to the supplier for further investigation at 62. Should there be no inconsistencies found, the tool continues with the test.

Following the assessment that the basic hardware and embedded software of the sound processor is in order, the tool then begins an assessment of the patient specific functions and data that are stored on the device. Whilst sound processors are typically constructed in such a way that they can be mass produced, all sound processors in use are specifically designed to take into consideration patient specific functions, data, and sound strategies, all of which are stored within the sound processor and form an integral part of the sound processor. Therefore should an individual use another person's sound processor with their own implant, they would experience a quite different hearing sensation, one not optimised with their own specific characteristics.

Accordingly, the next step 70 is to download the specific patient's individual strategies, functions, data and settings from an external source such as a floppy disk which the patient carries with them or via a global database that stores such information.

Once this data has been downloaded by the tool, the tool then checks at 80 whether the serial number embedded within this data matches with the serial number of the sound processor. Should there be an inconsistency with the serial number, the tool makes note of the problem and at 81 issues a warning to its user indicating that the recipient is using a sound processor that is not assigned to them.

Should the serial numbers agree, the tool makes a memory map sorting all the strategies, functions, data and settings retrieved from the external source and reference libraries provided with the tool, in the order as they appear in the sound processor's memory (ROM and RAM). This map is further referred to as the virtual memory map.

Next, an initial assessment of the patient specific data is performed at 90 which checks the stored values with design limits and notes any unusual values. The patient specific data or fitting data contains values which correspond to individual stimulation thresholds and comfort levels and should this information be incorrect malfunctions can occur due to incorrect fitting data. Even if the tool identifies any data that appears to be beyond the design limits the tool does not attempt to correct such data, but merely makes a note of the deviations at 91, and includes such matters in the final report.

At 100, the diagnosis tool compares the virtual memory map with the strategies, functions, data and settings as stored on the device. As the virtual memory map is indicative of what should be stored on the sound processor, derived from the most recent fitting session, and libraries, should there be an inconsistency between the two, the tool at 110 attempts to automatically correct this data in the sound processor. In the event that there is an inconsistency, the tool deletes the strategies, functions, data and settings stored on the sound processor and attempts a re-write of the data. At 111, a note is made of such corrections for inclusion in the final report. Following this re-write another comparison is performed at 120 to check whether the data does correspond. If there still exists an inconsistency with the data then the tool terminates the test and issues a fatal error warning at 121 stating that the memory in the sound processor is corrupt at a particular address and requires attention from the supplier at 122.

Should the correction be successful and both the virtual memory map and the data stored on the sound processor correspond, the tool will delete the data on the sound processor another two times but in different ways and each time re-write and compare with the virtual memory map once again. By doing so, sufficient confidence is built up to assess this initial data corruption as non repeatable and consequently the tool will determine that the sound processor may be released for further use. The test is then complete and a log is made available at 130 which provides a history of all tested functions and the changes made, together with any recommendations.

Depending on the user of the tool, the tool issues a report at an appropriate level for that user, on screen or by way of any other output device connected with the tool.

Depending upon this report the user either sends their sound processor to the clinic, agent, or first point of contact together with a copy of the report indicating the problem(s) found, or stores a copy of the report on the individual's file for future reference.

In any event the tool of the present embodiment of the present invention provides a thorough diagnostic and repair device which greatly improves the service that a clinician can provide to a cochlear implant patient, and reduces the time and effort that is required by the repair team of the device suppliers as they no longer are confronted with problems that require a minor correction, and are given a more detailed diagnosis of a problem which they can more clearly target.

As has been described, the present invention relates to an on-site and easily accessible tool, the strategy adopted in using the tool in diagnosing problems in a sound processor for a cochlear implant or the like, and to analysing, initialising, and loading recipient specific data into such a sound processor. Also the strategy to feedback the manufacturer of the sound processing device, and the means used by the tool fall under this disclosure.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A method of on-site diagnosis of a sound processor of an implantable prosthesis, the method comprising the steps of:
    testing functionality of a hardware component of the sound processor;
    determining whether patient-specific data stored by the sound processor is corrupted;
    assessing software functions of the sound processor; and
    generating a report on the sound processor performance based on one or more of the testing, the determining and the assessing.

2. The method of claim 1, wherein one or more steps are performed at a repair facility remote from the sound processor.

3. The method of claim 1 further comprising the step of restoring functionality of the sound processor.

4. The method of claim 3 wherein the step of restoring functionality of the sound processor comprises restoring software functions of the sound processor.

5. The method of claim 3 wherein the step of restoring functionality of the sound processor comprises restoring data stored by the sound processor.

6. The method of claim 1 wherein the step of generating a report on the performance of the sound processor comprises the steps of preparing an activity log containing information regarding one or more of performed functions, errors and warnings.

7. The method of claim 6 wherein the information contained in the activity log regarding the one or more of the performed functions, errors and warnings is at a level of detail corresponding to the identity of the recipient of the activity log.

8. The method of claim 1 further comprising the step of, prior to assessing and testing the sound processor, checking for updated assessment technology.

9. The method of claim 8 wherein the step of checking for updated assessment technology comprises checking for new data or new software functions to be installed to the sound processor.

10. The method of claim 1 further comprising the steps of retrieving a backup copy of patient data and replacing the patient data of the sound processor in the event of that patient data is determined to be corrupted in the sound processor.

11. The method of claim 10 wherein the step of retrieving a backup copy of patient data comprises retrieving the backup data from an external data storage medium.

12. The method of claim 11 wherein the external data storage medium is selected from the group consisting of a floppy disk, a CD ROM, a central data storage means, and a local data storage means.

13. The method of claim 10 wherein the step of retrieving a backup copy of patient data comprises retrieving the backup data over a communications network.

14. The method of claim 1 further comprising the step of reinstalling programming functions to the sound processor in the event of a programming function error in the sound processor.

15. The method of claim 14 wherein the programming functions are retrieved from an external data storage medium.

16. The method of claim 15, wherein the external data storage medium is selected from the group consisting of a floppy disk, a CD ROM, a central data storage means, and a local data storage means.

17. The method of claim 14 further comprising the step of, in the event of programming function error in the sound processor, referring the identified error to an implant manufacturer or repair facility and to a rehabilitation center associated with the recipient of the implant.

18. The method of claim 17 wherein in the event of detection that the programming functions of the sound processor deviate from the programming functions retrieved from any one of the data storage medium, central data storage means or local storage means, the method further comprises the steps of signalling warnings to the manufacturer or repair facility and to the rehabilitation center that the implant recipient is to consult an audiologist or clinician, and recommending that the sound processor not be sent to the repair facility.

19. A process for diagnosis and repair of a sound processor of an implanted prosthesis, the process comprising the steps of:
performing an on-site diagnosis of the sound processor using a recipient diagnosis and repair tool; and
repairing identified errors within the capability of the recipient diagnosis and repair tool.

20. The process of claim 19 wherein in the event of identifying an error which is not within the repair capability of the recipient diagnosis and repair tool, the process further comprises the step of performing an on-site diagnosis of the sound processor using a clinician diagnosis and repair tool.

21. The process of claim 20 further comprising the step of repairing identified errors within the capability of the clinician diagnosis and repair tool.

22. The process of claim 21 further comprising the step of providing the sound processor to a repair facility in the event of identifying an error which is not within the repair capability of the clinician diagnosis and repair tool.

23. A computer-readable media encoded with instructions operative to cause a computer to perform the steps of:
testing functionality of a hardware component of a sound processor of an implantable prosthesis;
determining whether patent-specific data stored by the sound processor is corrupted; and
assessing software functions of the sound processor.

24. The computer-readable media of claim 23 further encoded with instructions operative to cause a computer to perform the step of restoring functionality of the sound processor.

25. The computer-readable media of claim 24 wherein the step of restoring functionality of the sound processor comprises restoring software functions of the sound processor.

26. The computer-readable media of claim 24 wherein the step of restoring functionality of the sound processor comprises restoring data stored by the sound processor.

27. The computer-readable media of claim 23 further encoded with instructions operative to cause a computer to perform the step of generating a report on the performance of the sound processor.

28. The computer-readable media of claim 27 wherein the step of generating a report comprises the steps of assembling an activity log with performed functions, errors and warnings and reporting the activity log to a predetermined user.

29. The computer-readable media of claim 28 further encoded with instructions operative to cause a computer to perform the step of reporting the activity log at a level of detail corresponding to the identity of the predetermined recipient of the activity log.

30. The computer-readable media of claim 23 further encoded with instructions operative to cause a computer to perform the step of checking for updated assessment technology prior to assessing and testing the sound processor.

31. The computer-readable media of claim 30 wherein the step of checking for updated assessment technology comprises checking for new data or new software functions to be installed to the sound processor.

32. The computer-readable media of claim 23 further encoded with instructions operative to cause a computer to perform the steps of retrieving a backup copy of patient data and replacing the patient data of the sound processor in the event of patient data corruption in the sound processor.

33. The computer-readable media of claim 32 wherein the step of retrieving a backup copy of patient data comprises retrieving the backup data from an external data storage medium.

34. The computer-readable media of claim 33 wherein the step of retrieving a backup copy of patient data comprises retrieving the backup data from a central data storage means.

35. The computer-readable media of claim 32 wherein the step of retrieving a backup copy of patient data comprises retrieving the backup data from a local data storage means.

36. The computer-readable media of claim 32 wherein the step of retrieving a backup copy of patient data comprises retrieving the backup data over a communications network.

37. The computer-readable media of claim 23 further encoded with instructions operative to cause a computer to perform the step of reinstalling programming functions to the sound processor in the event of programming function error in the sound processor.

38. The computer-readable media of claim 37 wherein the programming functions are retrieved from a data storage medium, such as a floppy disk or CD-ROM, or from a central or local data storage means.

39. The computer-readable media of claim 37 further encoded with instructions operative to cause a computer to perform the step of providing instructions to send the prosthesis to an implant manufacturer or repair facility and to a rehabilitation center associated with the recipient of the implant in the event of programming function error in the sound processor.

40. The computer-readable media of claim 39 further encoded with instructions operative to cause a computer to perform the step of signaling warnings to the manufacturer or repair facility and to the rehabilitation centre that the implant recipient is to consult an audiologist or clinician, and recommending that the sound processor not be sent to the repair facility for unneeded repair in the event of detection that the programming functions of the sound processor deviate from the programming functions retrieved from any one of the data storage medium, central data storage means or local storage means.

* * * * *